US010123939B2

(12) United States Patent
Gobbi Frattini

(10) Patent No.: US 10,123,939 B2
(45) Date of Patent: Nov. 13, 2018

(54) HERMETIC CLOSING PLUG FOR A SEALED STERILE VIAL CONTAINING MEDICAL OR NUTRITIONAL ACTIVE SUBSTANCES, SUITABLE FOR THE STERILE CONNECTION TO A CONTAINER OF LIQUID DILUENT SOLUTION, AND STERILE CONNECTION SYSTEM USING SAID CLOSING PLUG

(71) Applicant: PAOLO GOBBI FRATTINI S.R.L., Milan (IT)

(72) Inventor: Paolo Giuseppe Gobbi Frattini, Sondalo SO (IT)

(73) Assignee: PAOLO GOBBI FRATTINI S.R.L., Milan (IT)

( * ) Notice: Subject to any disclaimer, the term of this patent is extended or adjusted under 35 U.S.C. 154(b) by 160 days.

(21) Appl. No.: 15/248,353

(22) Filed: Aug. 26, 2016

(65) Prior Publication Data

US 2017/0056288 A1 Mar. 2, 2017

(30) Foreign Application Priority Data

Aug. 27, 2015 (IT) ........................ 102015000046830

(51) Int. Cl.
*A61M 5/32* (2006.01)
*A61J 1/14* (2006.01)
(Continued)

(52) U.S. Cl.
CPC ........... *A61J 1/1412* (2013.01); *A61J 1/1406* (2013.01); *A61J 1/20* (2013.01); *B01L 3/50825* (2013.01);
(Continued)

(58) Field of Classification Search
CPC ...... A61J 1/1443; A61J 1/1406; A61J 1/1412; A61J 1/201; A61J 1/2048; B65D 51/002
See application file for complete search history.

(56) References Cited

U.S. PATENT DOCUMENTS 2,465,269 A 3/1949 Rhode et al.
3,792,794 A 2/1974 Cutter et al.
(Continued)

FOREIGN PATENT DOCUMENTS

EP 0 541 423 A1 5/1993

OTHER PUBLICATIONS

Italian Search Report, dated May 18, 2016 (2 pages).

*Primary Examiner* — Ariana Zimbouski
(74) *Attorney, Agent, or Firm* — Jacobson Holman, PLLC.

(57) ABSTRACT

A closing plug for a sealed sterile vial containing medical or nutritional active substances, which is suitable for the sterile connection to a container of liquid diluent solution. There is also described a sterile connection system between a sealed sterile vial closed by means of a plug and a tube for drawing said active substances, for mixing them with a liquid diluent solution inside a sterile container. The plug requires an internal sterile chamber in which, upon the piercing of an outer film for sealing the plug, a compressible protection cap of a piercing tip of the tube is inserted, which abuts against a seat of the sterile chamber allowing the tip to pierce the end wall of the protection cap and then the inner membrane of the closing plug. An intermediate pierceable membrane placed on the seat of the internal chamber of the vial may be included.

7 Claims, 5 Drawing Sheets

(51) Int. Cl.
*B01L 3/00* (2006.01)
*B65D 51/00* (2006.01)
*A61J 1/20* (2006.01)

(52) U.S. Cl.
CPC ............. *B65D 51/002* (2013.01); *A61J 1/201* (2015.05); *A61J 1/2055* (2015.05); *B01L 2300/044* (2013.01)

(56) References Cited

U.S. PATENT DOCUMENTS

| | | | | |
|---|---|---|---|---|
| 5,699,923 | A | 12/1997 | Burns | |
| 5,902,298 | A | 5/1999 | Niedospial, Jr. et al. | |
| 2012/0203138 | A1* | 8/2012 | Niunoya ............... | A61J 1/1406 600/576 |

* cited by examiner

HERMETIC CLOSING PLUG FOR A SEALED STERILE VIAL CONTAINING MEDICAL OR NUTRITIONAL ACTIVE SUBSTANCES, SUITABLE FOR THE STERILE CONNECTION TO A CONTAINER OF LIQUID DILUENT SOLUTION, AND STERILE CONNECTION SYSTEM USING SAID CLOSING PLUG

The present invention refers to a hermetic closing plug for a sealed sterile vial containing medical or nutritional active substances, in the form of powder or gel or another fluid, which is suitable for the sterile connection to a container of liquid diluent solution.

BACKGROUND OF THE INVENTION

The present invention also refers to a sterile connection system between a sealed sterile vial closed by means of the above-mentioned plug and a tube for drawing said active substances for mixing them with a liquid diluent solution maintained in sterile conditions inside a container.

In hospital environments, there is often a need to administer to patients, by infusion or internal instillation, medical or nutritional active substances of various type, which are made available separately, in particular in powder or gel form, inside suitable sealed sterile vials.

In order to make the active substances suitable for liquid instillation or infusion, a mixture comprising, in addition to the active substance, a liquid diluent solution needs to be formed.

Such a liquid solution is usually made available in sterile conditions inside a flexible bag, from which, in addition to a mixture delivery tube, a drawing and mixing tube extends, provided with a terminal to be attached to the vial containing the active substance and to pierce the closing plug thereof.

However, the problem of ensuring sterility conditions even during and after the attachment of the active substance vial to the drawing and mixing tube extending from the liquid diluent solution bag still remains.

Any loss of sterility, in particular in the case of high-risk drugs, may lead to severe effects for both the patient and the healthcare personnel responsible for the patient care.

U.S. Pat. No. 5,699,923 A describes a hermetic closing plug for a sealed vial with internal sterile chamber for containing medical or nutritional active substances. The plug is suitable for the connection to a drawing and mixing tube which extends from a liquid diluent solution container and is provided with a terminal to be attached to the vial with a hollow tip for piercing the plug. The hollow tip is protected by a cap made of an axially compressible material capable of piercing an outer film or membrane for sealing the plug.

BRIEF SUMMARY OF THE INVENTION

It is the object of the present invention to provide a sealed hermetic closing plug for a vial containing medical or nutritional active substances and a sterile connection system between the internal sterile chamber of said vial and a tube for drawing and mixing said active substances with a liquid diluent solution maintained in sterile conditions inside a container, which ensures perfect sterility conditions during the whole process of attaching the vial to the drawing and mixing tube.

According to a first aspect, this object is achieved by means of a hermetic closing plug for a sealed vial with internal sterile chamber for containing medical or nutritional active substances, suitable for the connection to a drawing and mixing tube extending from a liquid diluent solution container and provided with a terminal to be attached to the vial with a hollow tip for piercing the plug, protected in a sterile manner by a cap made of an axially compressible material adapted to pierce the outer sealing film or membrane of the plug, characterized in that it comprises an internal sterile chamber located between said outer sealing film or membrane and an inner pierceable membrane arranged to close the internal chamber of the vial hermetically, wherein:

- said internal sterile chamber of the closing plug includes an abutment seat for the end of said compressible cap once the outer sealing film or membrane of the plug has been pierced and a passage of communication with said at least one inner pierceable membrane to allow, in a final step of hooking the terminal of the tube for the connection to the head of the vial, the axial compression of said compressible cap and the further advancement of said piercing tip for piercing the end of said compressible cap and subsequently said inner pierceable membrane of the plug of the vial for putting the internal chamber of the vial in sterile communication with said drawing and mixing tube.

According to a further aspect, the stated objects is achieved by a sterile connection system defined in claim 1, between an internal sterile chamber of a vial containing medical or nutritional active substances and a tube for drawing said active substances for mixing them with a liquid diluent solution, wherein:

- the vial has a head provided with a hermetic closing plug made of a pierceable plastic material over which an outer pierceable sealing film or membrane is placed, being adapted to maintain the plug in sterile conditions;
- the drawing tube has a hollow piercing tip which extends coaxially into a terminal for the attachment to the head of the vial and is provided with a protection cap adapted to maintain said piercing tip in sterile conditions;

characterized in that:

- said protection cap is made of an axially compressible material with such a compression resistance to allow the cap to pierce said outer sealing film or membrane of the plug of the vial in a first step of advancing the terminal of the tube for the connection to the head of the vial;
- said closing plug is made of a plastic material with a rigidity higher than that of said compressible cap and has an internal sterile chamber located between said outer sealing film or membrane and an inner pierceable membrane arranged to close the internal chamber of the vial hermetically;
- said internal sterile chamber of the closing plug includes an abutment seat for the end of said compressible cap in a second step of advancing the terminal of the tube for the connection to the head of the vial upon the piercing of the outer sealing film or membrane of the plug, and a passage of communication with said at least one inner pierceable membrane to allow, in a final step of hooking the terminal of the tube for the connection to the head of the vial, the axial compression of said compressible cap and the further advancement of said piercing tip for piercing the end of said compressible cap and subsequently said inner pierceable membrane of the plug of the vial for putting the internal chamber of the vial in sterile communication with said drawing and mixing tube.

Advantageously, said closing plug of the vial may include a further pierceable membrane or intermediate membrane arranged at the entrance of said passage of communication with said at least one inner pierceable membrane.

Preferably, said closing plug of the vial is made of thermoplastic material.

In turn, the outer sealing film or membrane of the vial may be made of medical paper, thermoplastic material, rubber, silicone, thin aluminum or other suitable easily pierceable material. Optionally, it may be in one piece with the closing plug.

In turn, the intermediate membrane, when included, may be made of a similar material, even in one piece with the closing plug.

In turn, the compressible protection cap of the piercing tip of the drawing and mixing tube may be made of rubber, silicone or other compressible material, as long as it is provided with a pierceable end wall.

BRIEF DESCRIPTION OF THE SEVERAL VIEWS OF THE DRAWINGS

The features of the present invention will become more apparent by means of the following detailed description of two practical embodiments shown by way of example in the accompanying drawings, in which.

DETAILED DESCRIPTION OF THE INVENTION

Figure 1:
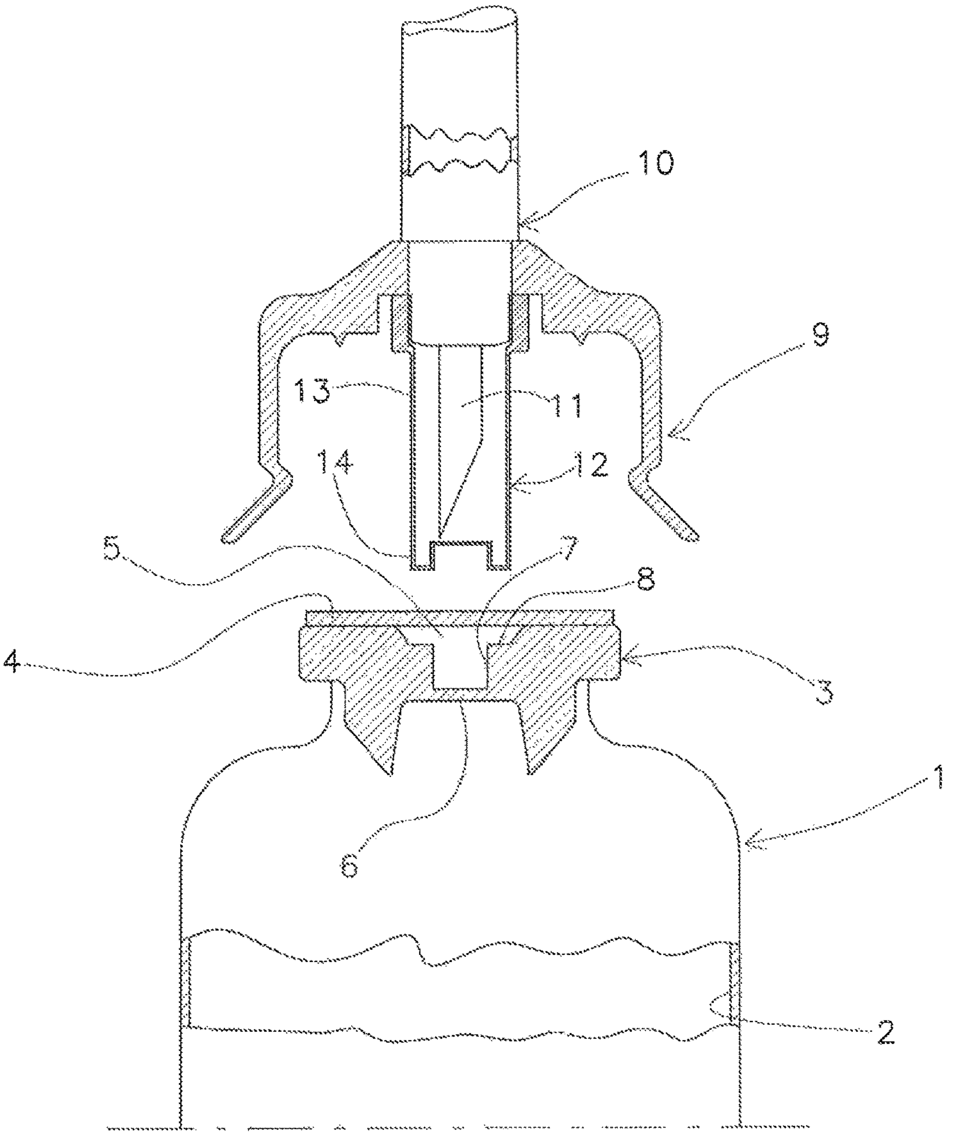
FIG. 1 shows, as a whole and in rest conditions, a sterile connection system according to the present invention between an active substance vial provided with a closing plug according to the present invention and a tube for drawing and mixing said active substances with a liquid diluent solution.

FIG. 1 shows the portion of head of a vial 1 with an internal sterile chamber 2 for containing medical or nutritional active substances. Vial 1 is hermetically closed with a closing plug 3 made of a thermoplastic material over which a thin outer sealing film or membrane 4 made of medical paper, thermoplastic material, rubber, silicone, thin aluminum or other suitable easily pierceable material is placed and fixed, possibly in one piece with the closing plug (3).

The closing plug 3 has an internal sterile chamber 5 between the outer sealing film or membrane 4 and an inner pierceable membrane 6, in one piece with the rest of plug 3, which is arranged to close the lower end of a passage 7 of communication between the internal sterile chamber 5 of plug 3 and the internal sterile chamber 2 of vial 1. An annular face or seat 8 surrounds the upper end of passage 7.

FIG. 1 also shows the attachment terminal or portion 9 of a drawing and mixing tube 10 which extends from a conventional bag or other container for sterilely housing a liquid diluent solution (not seen in the drawing). Inside the attachment terminal 9, the drawing and mixing tube 10 ends with a hollow piercing tip 11 in communication with the tube itself. The piercing tip 11 is protected in a sterile manner by a cylindrical cap 12 made of an axially compressible material capable of piercing the outer sealing film or membrane 4 but not the thermoplastic material of plug 3. The protection cap 12 is closed at the bottom by a pierceable end wall 13, surrounded by an annular projection 14.

The assembly in FIG. 1 allows the sterile connection between the internal chamber 2 of the vial and the internal chamber (not shown) of the container of liquid diluent solution as described below with reference to FIGS. 2, 3 and 4.

In a first operating step (FIG. 2), the attachment terminal 9 of the drawing and mixing tube 10 is brought forward but not yet attached to the head of vial 1. The advancement determines the piercing of the outer sealing film or membrane 4 by the protection cap 12, the end thereof penetrates into the inner sterile chamber 5 of plug 3 until it abuts, without compressing, against the annular projection 14 thereof on the annular face or seat 8 of said sterile chamber.

Continuing the advancement of the attachment terminal 9 towards the head of the vial (FIG. 3), the protection cap 12 of the piercing tip 11 axially compresses due to the abutment thereof with the annular face or seat 8, allowing the piercing tip 11 to pierce the end wall 13 of the protection cap 12 and enter the passage 7 which leads to the inner protection membrane 6 of plug 3.

When the attachment terminal 9 attaches to the head of vial 1 (FIG. 4), the protection cap 12 is further compressed and the piercing tip 11 penetrates through the inner membrane 6, thus putting the internal chamber of vial 1 in sterile communication with the interior of the drawing and mixing tube 10, and therefore with the internal sterile chamber of the container of liquid diluent solution.

Figure 2:
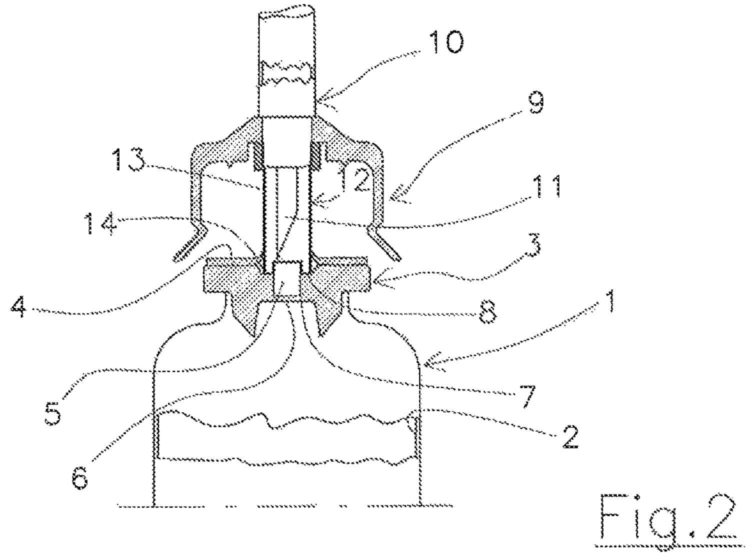
FIGS. 2-4 sequentially show the steps of attaching and piercing the closing plug of the vial.
Figure 3:
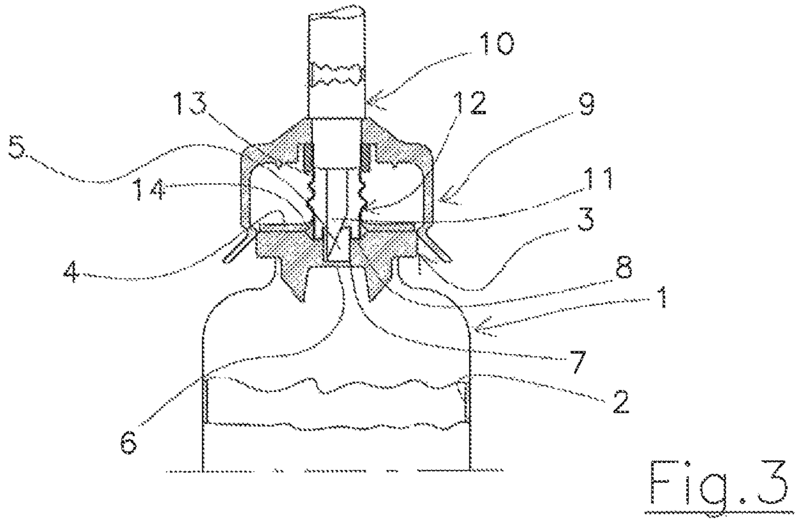
Figure 4:
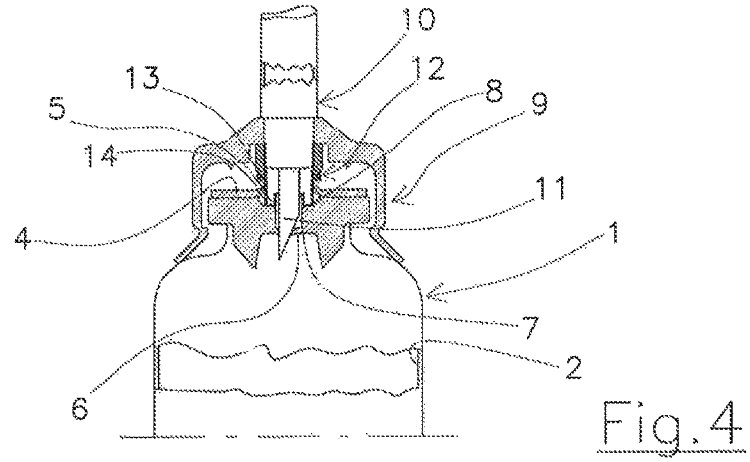

As described and shown in FIGS. 2-4, it is apparent that the whole operation of attaching and putting into communication takes place without any loss of sterility.

Figure 5:
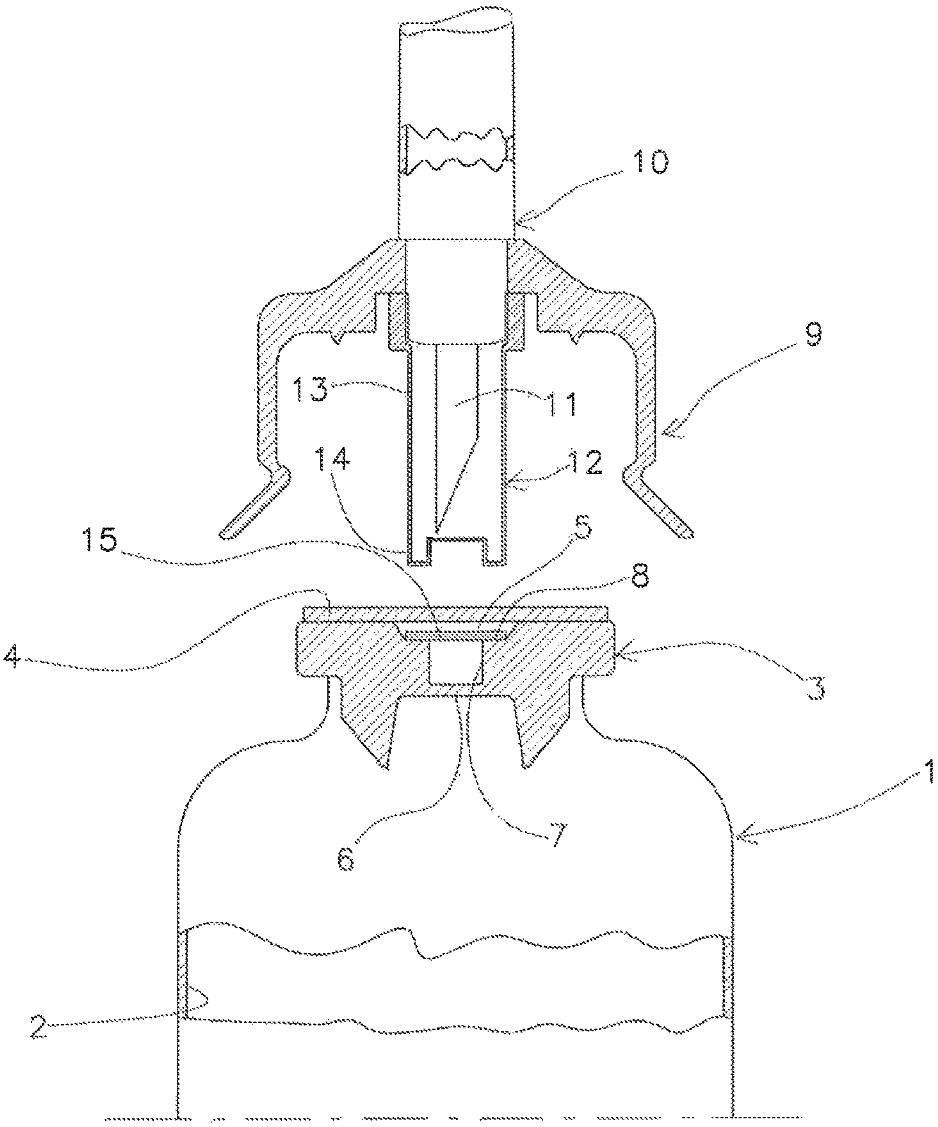
FIG. 5 shows, as a whole and in rest conditions, a variant of the sterile connection system according to the present invention, in which the closing plug of the vial is provided with an inner protection membrane or intermediate membrane made of a pierceable material.

The assembly in FIG. 5 is the same as that in FIG. 1 except that a further internal protection membrane or intermediate membrane 15 is provided, made of a pierceable material, for example medical paper, thermoplastic material, rubber, silicone, thin aluminum or other suitable easily pierceable material, possibly in one piece with the closing plug (3). The intermediate membrane 15 is placed on the annular face or seat 8.

Figure 6:
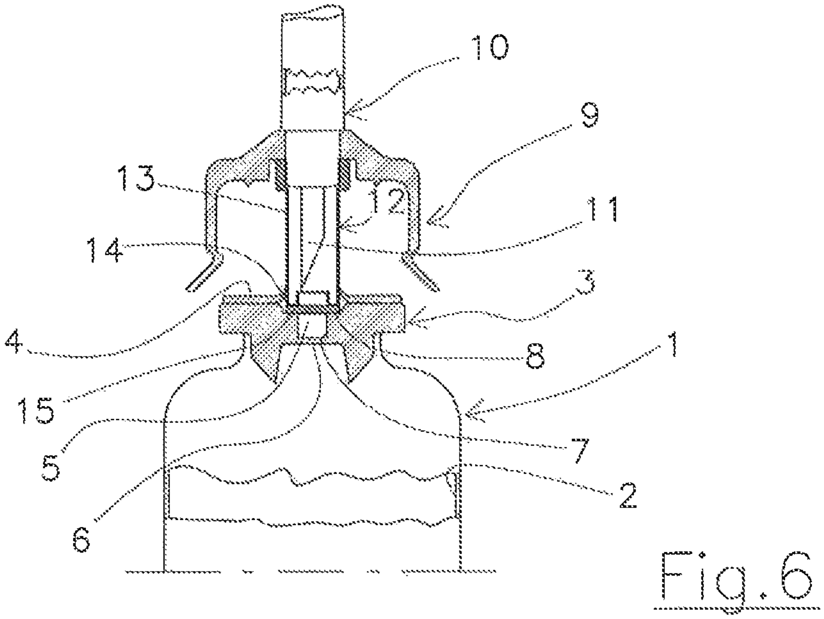
FIGS. 6-9 sequentially show the steps of attaching and piercing the closing plug of the vial according to the variant in FIG. 5.
Figure 7:
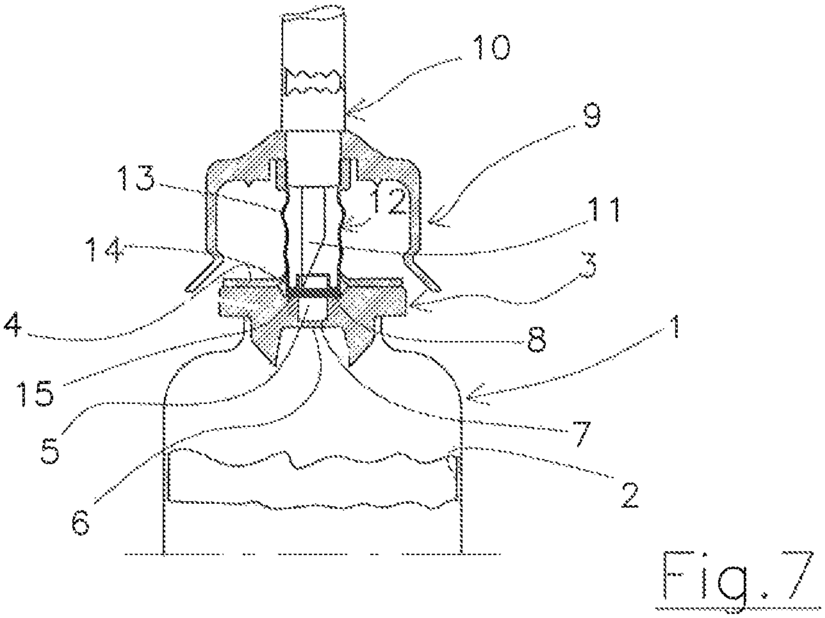
Figure 8:
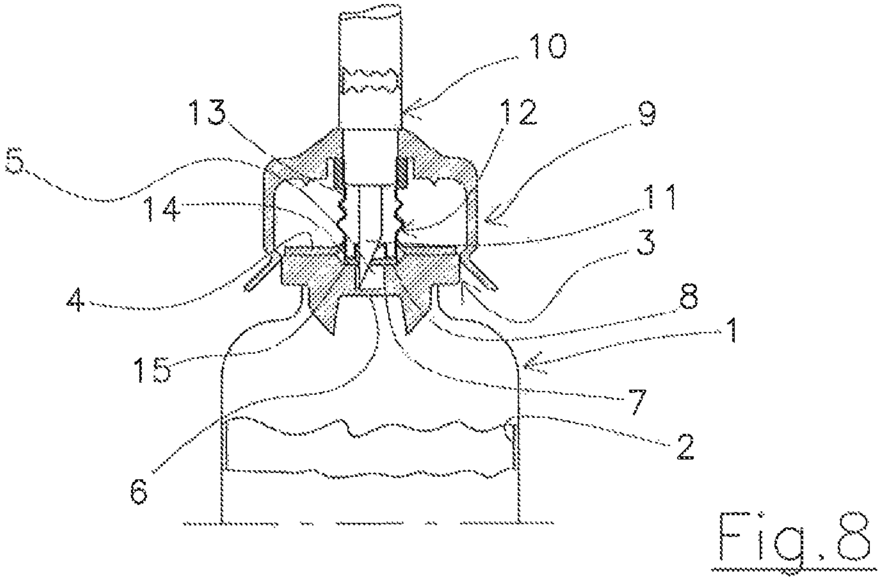
Figure 9:
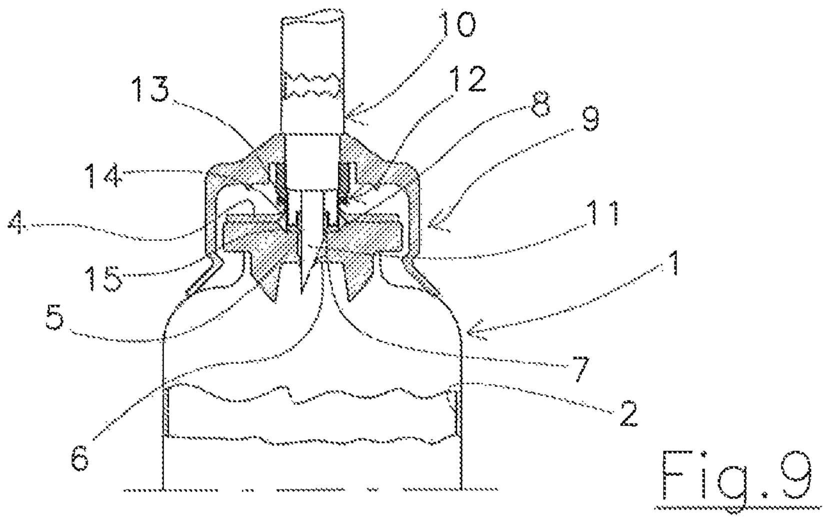

In this case, upon the piercing of the outer sealing film or membrane 4, the annular projection 14 of the terminal end of the protection cap 12 abuts against the intermediate membrane 15 (FIG. 6) and, continuing the advancement of the attachment terminal 9 towards the head of vial 1, axially compresses' and is then pierced by the piercing tip 11, which continues piercing the intermediate membrane 15 and then the internal membrane 6 as shown in FIGS. 7, 8 and 9.

Also in this case, the whole operation of attaching and putting into communication takes place without any loss of sterility.

The invention claimed is:

1. A sterile connection system between an internal sterile chamber of a vial for containing medical or nutritional active substances and a tube for drawing said active substances and mixing them with a liquid diluent solution maintained in sterile conditions in a container, wherein:

the vial has a head provided with a hermetic closing plug of a pierceable plastic material on which an outer pierceable sealing film or membrane is placed which is capable of maintaining the closing plug in sterile conditions;

the tube has a hollow piercing tip which extends coaxially inside a terminal for attachment to the head of the vial and is provided with a compressible protection cap able to keep said piercing tip in sterile conditions;

wherein said compressible protection cap is made of axially compressible material with such a compression resistance to allow the compressible protection cap to pierce said outer sealing film or membrane of the closing plug of the vial in a first advancement step of the terminal of the tube to the head of the vial;

said closing plug is made of a plastic material having a higher rigidity than said compressible protection cap and has an internal sterile chamber located between said outer sealing film or membrane and an inner pierceable membrane arranged to close hermetically the internal sterile chamber of the vial;

said internal sterile chamber of the closing plug includes a seat for abutment of the end of said compressible protection cap in a second step of advancement of the terminal of the tube to the head of the vial after piercing of the outer sealing film or membrane of the closing plug and a passage of communication with said inner pierceable membrane to allow, in a final step of hooking of the terminal of the tube to the head of the vial, axial compression of said compressible protection cap and further advancement of said piercing to pierce the end of said compressible protection cap and then said inner piercable membrane of the closing plug of the vial to put in sterile communication the internal sterile chamber of the vial and said tube.

2. The sterile connection system according to claim 1, wherein said closing plug of the vial comprises a further internal or intermediate pierceable membrane placed on said seat of the internal sterile chamber of the closing plug.

3. The sterile connection system according to claim 1, wherein said plastic material of said closing plug is a thermoplastic material.

4. The sterile connection system according to claim 3, wherein said internal pierceable membrane is in one piece with the closing plug.

5. The sterile connection system according to claim 1, wherein said outer sealing film or membrane of the closing plug is made of medical paper, thermoplastic material, rubber, silicone, or thin aluminum in one piece with the closing plug.

6. The sterile connection system according to claim 1, wherein said compressible protection cap of the piercing tip of the tube is made of rubber or silicone with a pierceable end wall.

7. The sterile connection system according to claim 2, wherein said further internal or intermediate pierceable membrane is made of medical paper, thermoplastic material, rubber, silicone, or thin aluminum, in one piece with the closing plug.

* * * * *